United States Patent
Pellegrini et al.

(10) Patent No.: US 9,480,557 B2
(45) Date of Patent: Nov. 1, 2016

(54) STENTS FOR PROSTHETIC HEART VALVES

(75) Inventors: Gianfranco M. Pellegrini, Santa Rosa, CA (US); Mike Krivoruchko, Forestville, CA (US); Finn O. Rinne, Santa Rosa, CA (US); Matthew J. Rust, Windsor, CA (US)

(73) Assignee: Medtronic, Inc., Minneapolis, MN (US)

( * ) Notice: Subject to any disclaimer, the term of this patent is extended or adjusted under 35 U.S.C. 154(b) by 643 days.

(21) Appl. No.: 13/071,274

(22) Filed: Mar. 24, 2011

(65) Prior Publication Data
US 2011/0238168 A1  Sep. 29, 2011

Related U.S. Application Data

(60) Provisional application No. 61/317,459, filed on Mar. 25, 2010.

(51) Int. Cl.
*A61F 2/82* (2013.01)
*A61F 2/24* (2006.01)

(52) U.S. Cl.
CPC ........... *A61F 2/2412* (2013.01); *A61F 2/2418* (2013.01); *A61F 2230/008* (2013.01); *A61F 2230/0054* (2013.01); *A61F 2230/0067* (2013.01); *A61F 2230/0078* (2013.01); *A61F 2250/0036* (2013.01); *A61F 2250/0039* (2013.01)

(58) Field of Classification Search
CPC .................................... A61F 2/24; A61F 2/82
USPC ................................................ 623/2.17, 1.26
See application file for complete search history.

(56) References Cited

U.S. PATENT DOCUMENTS

| | | | |
|---|---|---|---|
| 3,671,979 | A | 6/1972 | Moulopoulos |
| 4,056,854 | A | 11/1977 | Boretos et al. |
| 4,994,077 | A | 2/1991 | Dobben |
| 5,332,402 | A | 7/1994 | Teitelbaum |
| 5,370,685 | A | 12/1994 | Stevens |
| 5,397,351 | A | 3/1995 | Pavcnik et al. |
| 5,554,185 | A | 9/1996 | Block et al. |
| 5,855,601 | A | 1/1999 | Bessler et al. |
| 6,168,614 | B1 | 1/2001 | Andersen et al. |
| 2003/0199963 | A1 | 10/2003 | Tower et al. |

(Continued)

FOREIGN PATENT DOCUMENTS

| | | |
|---|---|---|
| WO | WO2006/127765 | 11/2006 |
| WO | WO2007/130537 | 11/2007 |
| WO | WO2009/094188 | 7/2009 |

OTHER PUBLICATIONS

Andersen, H.R. et al, "Transluminal implantation of artificial heart valves. Description of a new expandable aortic valve and intial results with implantation by catheter technique in closed chest pigs." Euro. Heart J. (1992) 13:704-708.

(Continued)

*Primary Examiner* — Matthew Schall

(57) ABSTRACT

A prosthetic valve including a wire frame having a generally tubular body portion, an interior area, a longitudinal axis, a first end comprising a plurality of crowns, and a second end comprising a greater number of crowns than the first end. The wire frame includes a plurality of adjacent rows of modified diamond-shaped structures extending between the first and second ends. The prosthetic valve further includes a valve structure that includes a plurality of leaflets and that is attached within the interior area of the wire frame.

20 Claims, 10 Drawing Sheets

(56) References Cited

U.S. PATENT DOCUMENTS

| | | |
|---|---|---|
| 2003/0199971 A1 | 10/2003 | Tower et al. |
| 2004/0034411 A1 | 2/2004 | Quijano et al. |
| 2009/0216312 A1 | 8/2009 | Straubinger et al. |
| 2009/0287299 A1* | 11/2009 | Tabor et al. ................ 623/1.26 |

OTHER PUBLICATIONS

Anderson, J. R., et al., "Transluminal Catheter Implantation of New Expandable Artificial Cardiac Value", EUR Heart J., 1990, 11: (Suppl) 224a.

Block P C, "Clinical and Hemodyamic Follow-Up After Percutaneous Aortic Valvuloplasty in the Elderly", The American Journal of Cardiology, vol. 62, Oct. 1, 1998.

Bonhoeffer, et al, "Percutaneous Insertion of the Pulmonary Valve," Journal of the American College of Cardiology (United States), May 15, 2002, pp. 1664-1669.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Stpes Toward Percutaneous Aortic Valve Replacement," Circulation (United States), Feb. 12, 2002, pp. 775-778.

Boudjemline, et al, "Percutaneous Implantation of a Valve in the Descending Aorta in Lambs," European Heart Journal (England), Jul. 2002, pp. 1045-1049.

Cribier, A. et al, "Percutaneous Transcatheter Implantation of an Aortic Valve Prosthesis for Calcific Aortic Stenosis: First Human Case Description," Circulation (2002) 3006-3008.

Hilbert S. L., "Evaluation of Explanted Polyurethane Trileaflet Cardiac Valve Prosthesis", J Thorac Cardiovascular Surgery, 1989; 94:419-29.

Kulkinski, D., "Future Horizons in Surgical Aortic Valve Replacement: Lessons Learned Duriing the Early Stages of Developing a Transluminal Implantation Technique", ASAIO J, 2004; 50:364-68.

\* cited by examiner

STENTS FOR PROSTHETIC HEART VALVES

PRIORITY CLAIM

This application claims the benefit of U.S. Provisional Patent Application Ser. No. 61/317,459, filed Mar. 25, 2010, and titled "STENTS FOR PROSTHETIC HEART VALVES", the entire disclosure of which is incorporated herein by reference.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously-delivered prosthetic heart valves have been suggested having a generally similar configuration, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a continued desire to provide different designs of cardiac valves that can be implanted in a minimally invasive and percutaneous manner.

SUMMARY

The replacement heart valves of the invention each include a stent to which a valve structure is attached. The stents of the invention include a wide variety of structures and features that can be used alone or in combination with features of other stents of the invention. Many of the structures are compressible to a relatively small diameter for percutaneous delivery to the heart of the patient, and then are expandable either via removal of external compressive forces (e.g., self-expanding stents), or through application of an outward radial force (e.g., balloon expandable stents). The delivery systems described herein can be used to deliver stents, valved stents, or other interventional devices such as ASD (atrial septal defect) closure devices, VSD (ventricular septal defect) closure devices, or PFO (patent foramen ovale) occluders.

Methods for insertion of the replacement heart valves of the invention include delivery systems that can maintain the stent structures in their compressed state during their insertion and allow or cause the stent structures to expand once they are in their desired location. The methods of the invention may include implantation of the stent structures using either an antegrade or retrograde approach. Further, in many of the delivery approaches of the invention, the stent structure is rotatable in vivo to allow the stent structure to be positioned in a desired orientation.

The stent structures of the invention provide for reduced crown density at one end of the stent, along with other structural features that provide for a relatively low crimp profile and help to minimize tissue pressure during the crimping or stent compression process. In addition, features of embodiments of the stents of the invention can prevent or minimize buckling of the stent while maintaining columnar support for the stent, such as during deployment thereof.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
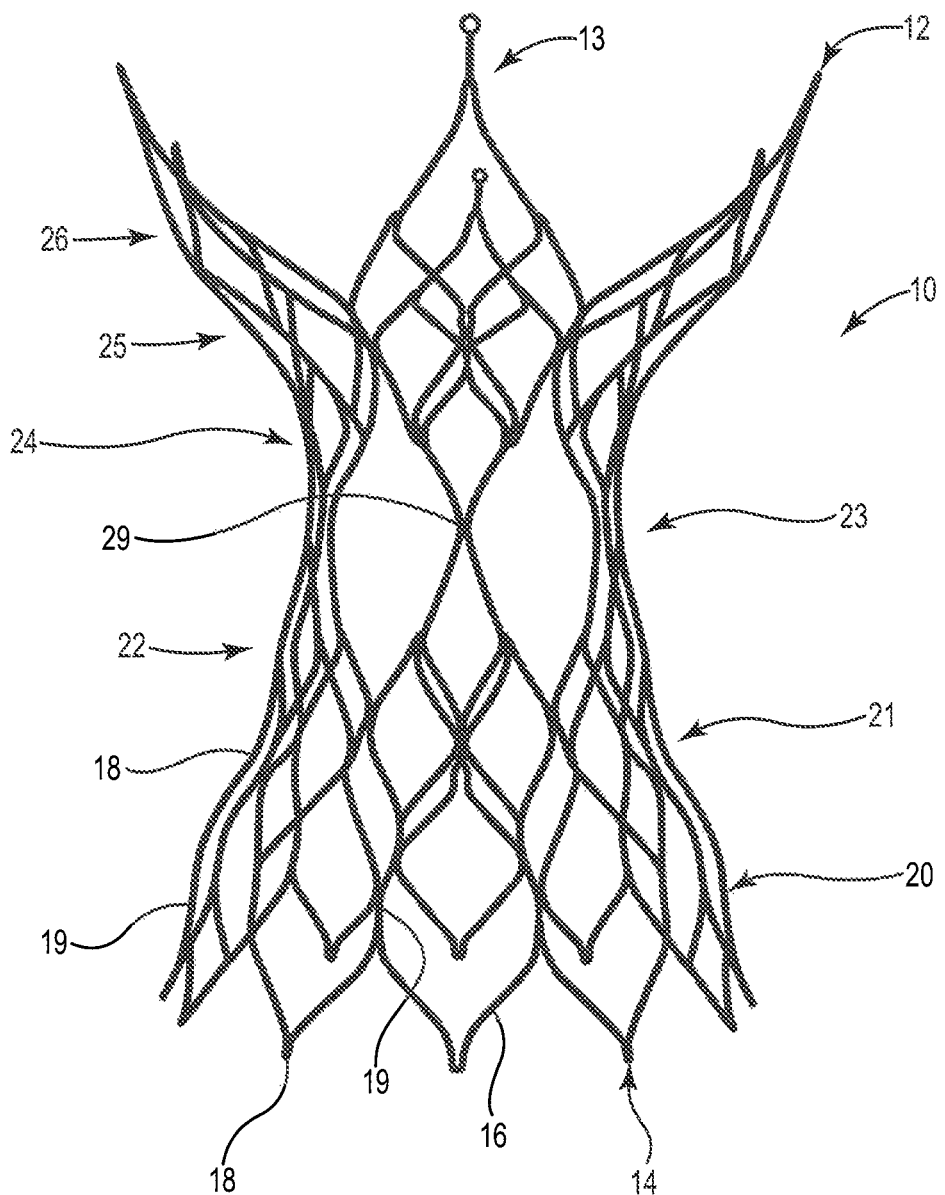
FIG. 1 is a front view of an embodiment of a stent in accordance with the invention.

As referred to herein, the prosthetic heart valves used in accordance with various devices and methods of heart valve delivery may include a wide variety of different configurations, such as a prosthetic heart valve having tissue leaflets or a synthetic heart valve having polymeric, metallic, or tissue-engineered leaflets, and can be specifically configured for replacing any heart valve. In addition, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example.

Although each of the stents described herein will typically include leaflets attached within an internal stent area, the leaflets are not shown in many of the illustrated embodiments for clarity purposes. In general, the stents described herein include a support structure comprising a number of strut or wire portions arranged relative to each other to provide a desired compressibility, strength, and leaflet attachment zone(s) to the heart valve. Other details on particular configurations of the stents of the invention are also described below; however, in general terms, stents of the invention are generally tubular support structures, and leaflets will be secured within the internal area of the support structure to provide a valved stent. The leaflets can be formed from a variety of materials, such as autologous tissue, xenograph material, or synthetics, as are known in the art. The leaflets may be provided as a homogenous, biological valve structure, such as a porcine, bovine, or equine valve. Alternatively, the leaflets can be provided as independent structures (e.g., as can be formed with bovine or equine pericardial leaflets) and subsequently assembled to the support structure of the stent. In another alternative, the stent and leaflets can be fabricated at the same time, such as may be accomplished using high strength nano-manufactured NiTi films of the type produced at Advanced Bio Prosthetic Surfaces Ltd. (ABPS) of San Antonio, Tex., for example. The support structures are generally configured to accommodate three leaflets; however, the replacement prosthetic heart valves of the invention can incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets utilize certain features of known expandable prosthetic heart valve configurations, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodynamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000:102:813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. In some embodiments, when aligning the stents of the invention with native anatomical structures, they are aligned so as to not block the coronary arteries, and native mitral or tricuspid valves are aligned relative to the anterior leaflet and/or the trigones/commissures.

Some embodiments of the support structures of the stents described herein can be a series of wires or wire segments arranged so that they are capable of transitioning from a collapsed state to an expanded state. In some embodiments, a number of individual wires comprising the support structure can be formed of a metal or other material. These wires are arranged in such a way that a support structure allows for folding or compressing to a contracted state in which its internal diameter is greatly reduced from its internal diameter in an expanded state. In its collapsed state, such a support structure with attached valves can be mounted relative to a delivery device, such as a balloon catheter, for example. The support structure is configured so that it can be changed to its expanded state when desired, such as by the expansion of a balloon catheter. The delivery systems used for such a stent should be provided with degrees of rotational and axial orientation capabilities in order to properly position the new stent at its desired location.

The wires of the support structure of the stents in other embodiments can instead be formed from a shape memory material such as a nickel titanium alloy (e.g., Nitinol) or a very high-tensile material that will expand from its compressed state to its original state after removal of external forces. With this material, the support structure is self-expandable from a contracted state to an expanded state, such as by the application of heat, energy, and the like, or by the removal of external forces (e.g., compressive forces). This support structure can be repeatedly compressed and re-expanded without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand. Alternatively, the stent structures of the invention can be implanted using conventional surgical techniques and/or minimally invasive surgical procedures. In such cases, the stents of the invention can advantageously require relatively few or no sutures to secure the stent to an anatomical location within the patient.

Referring now to the Figures, wherein the components are labeled with like numerals throughout the several Figures and initially to FIGS. 1 and 2a-2c, stents 10, 30, 32, and 34, respectively, are illustrated. Initially referring to FIG. 1, stent 10 includes a first end 12 having six crowns and a second end 14 having twelve crowns. In this embodiment, the first end 12 may be considered to be the outflow end of the stent and the second end 14 may be considered to be the inflow end of the stent, although it is contemplated that the first end 12 is the inflow end of the stent and that the second end 14 is the outflow end of the stent. At least one of the stent crowns at the first end 12 includes a crown end 13 that may include a half-dome or tee connector, as will be described below relative to FIGS. 6 and 7, for example. These crown ends 13 can be used for attachment to a delivery system, for example. It is contemplated that each of the crown ends 13 at the second end includes a half-dome or tee connector, as shown, or that only some of the crowns include such a connector. The size and shape of the crown ends 13 can all be the same on a single stent, or they can instead have different sizes and/or shapes.

Stent structure 10 generally includes a series of modified diamond-like structures arranged in adjacent rows, where each of the diamond structures or shapes is defined, by a series of wires or wire segments. Due to the diamond shape of these structures, at least one "peak" of each diamond-shaped structure of one row coincides with a "valley" created by two circumferentially adjacent diamond-shaped structures in an adjacent row. That is, a single row of diamond-shaped structures can be defined by multiple diamond-shaped structures that are circumferentially adjacent to each other around the stent and that are spaced at a similar longitudinal distance relative to the stent ends. Further, the phrase "adjacent row" used herein refers to a row of diamond structures that is located closest to, or interconnecting or overlapping with, another row of diamond structures along the longitudinal direction of the stent.

The references herein to "diamond" shaped structures are intended to refer generally to the four-sided shapes illustrated, which can include straight, curved, and/or a combination of straight and curved wire segments. The diamond shape structures further include intersection points or base areas where each two adjacent wires or wire segments meet. It is understood that these intersection points or base areas can be generally curved or include a radius, as shown, or that the intersection points can include sharper angles between wire segments. As shown in FIG. 1, each diamond structure includes two intersection points that are spaced from each other along the length of the stent 10, which can be referred to as "peaks". The diamond structures further include two intersection points that are spaced from each other in the circumferential direction of the stent 10. It is noted also this description is meant to be general relative to the diamond shape of the structures in that it is contemplated that each of the structures can include wires that are curved or otherwise contoured such that sharp intersection points are not created between wires or wire segments. In such cases, a change of curvature of a wire segment can be considered to be a defining point between sides of a diamond-shaped structure.

It is further noted that the entire stent may be made of a single piece of material, such that reference herein to wires or wire segments is intended to encompass certain portions of the shapes rather than actual separate pieces of wire that are attached to each other. In other embodiments, multiple wire segments can be arranged and attached to provide the desired stent structure.

With reference to one exemplary diamond-shaped structure 16 of stent 10, the intersection points that are spaced from each other along the length of the stent are illustrated as intersection points or peaks 18, while the intersection points that are spaced from each other relative to the circumference of the stent 10 are illustrated as intersection points or areas 19. As can also be seen in FIG. 12, the intersection points of a stent of the invention can be spaced from each other in a direction that is generally parallel to a longitudinal axis of the stent 10, although it is contemplated that the intersection points are spaced from each other in a direction that is not parallel to this longitudinal axis.

As described above relative to FIG. 1, the structure of stent 10 includes a series of adjacent rows of diamond-shaped structures. In particular, stent 10 includes a row 20 of such structures at second end 14 of the stent, wherein this particular embodiment includes twelve diamond-shaped structures in row 20. A row 21 of diamond-shaped structures is adjacent to row 20 and also includes twelve diamond-shaped structures, wherein each of the structures of row 21 shares at least a portion of two wire segments with structures of row 20. The next row 22 is adjacent to row 21 and includes six diamond-shaped structures, which are spaced from each other around the circumference of stent 10 in such a way that they do not touch each other. Each of these structures of row 22 shares two wire segments with the structures of adjacent row 21.

A row 23 of wire structures is adjacent to row 22 and includes six diamond-shaped structures that are shown in this embodiment as being relatively elongated along the length of the stent 10, and therefore have a somewhat larger central area than the structures of the other rows of this embodiment. Each of these structures of row 23 shares two wires segments with structures of adjacent row 22. Row 23 further includes connector portions or crowns 29 between adjacent structures of this row. These crowns 29 can be made of the same or a different material from that of the wires of the stent. Another row 24 of wire structures is adjacent to row 23 and includes six diamond-shaped structures that can be the same or similar and size and shape to the wire structures of row 22 or that can have differently sized and/or shaped wire structures to those of row 22. Again, each of these wire structures of row 24 shares two wire segments with structures of adjacent row 23. The crowns or connector portions 29 are structural features that essentially connect or bridge the peaks of the structures of rows 22 and 24, in addition to connecting or bridging adjacent wire structures of row 23. Another row 25 of wire structures is adjacent to row 24 and includes twelve diamond-shaped structures, where each of the structures shares two sides with an adjacent structure in row 24. The final row of structures is row 26, which is positioned at first end 12 of stent 10. Row 26 includes six diamond-shaped structures, as described above.

With this reduction in the number of structures in the more central area of the stent (and corresponding crowns or peaks of these structures) as compared to the number of structures at the second end 14 of the stent, for example, the open cell area is increased when the device is placed in the intended anatomical position within the patient. This can provide some or all of the following advantages: increased percutaneous coronary intervention (PCI) access; increased perfusion to the coronaries, which can improve blood flow; a greater crimped cell area to prevent or minimize pinching of tissue between struts; and a reduction in the accumulated volume (i.e., less metal) for the crimping operation, thereby providing increased packing efficiency. In addition, these structures have been designed to generally follow the valve design, specifically at the commissural junction. The inner crown radius, or intrados, can be provided with an appropriate size to allow tissue to prolapse or extend through the cell when the stent is in its crimped condition.

In FIG. 1, stent 10 is illustrated in its expanded or partially expanded condition. This illustrated condition is intended to represent the general stent condition when it is implanted within the anatomy of a patient. In this expanded condition, stent 10 is generally configured to have a relatively small diameter in the central area as compared to the diameter of its ends 12, 14. That is, the area of row 23 has a smaller diameter than the diameters of the flared ends 12, 14. End 12 can have the same or different diameter in its expanded condition as the diameter of end 14. The outward flares at the ends 12, 14 of the stent 10 (i.e., away from the central longitudinal axis of the stent) can prevent or minimize leakage between the implanted heart valve and the native annulus and/or to provide a physical and/or visual docking feature to secure the stent against a wall of a vessel or opening in the heart to prevent migration of the stent, for example.

Figures 2A, 2B, 2C:
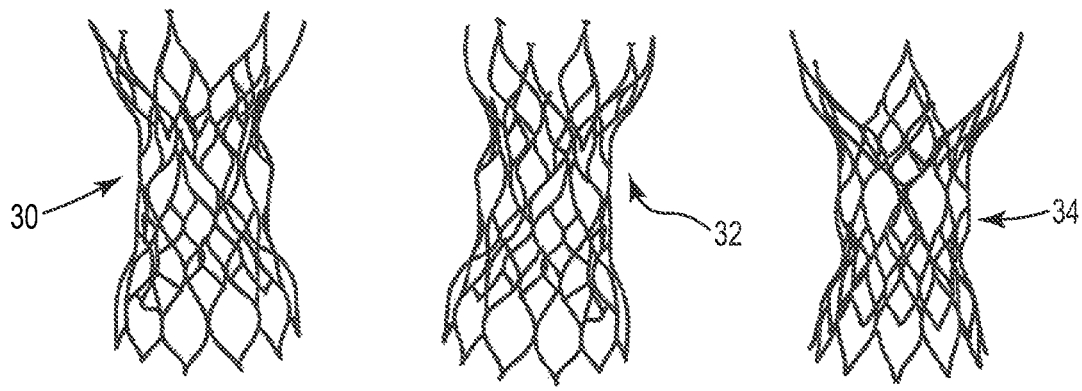
FIGS. 2a-2c are front views of three exemplary stents in accordance with the invention.

Exemplary stents 30, 32, and 34 of FIGS. 2a-2c are similar to stent 10 of FIG. 1. These figures are provided for additional views of stents that include the same number of rows of diamond-shaped segments and the like as the stent 10 of FIG. 1, wherein portions of stents 30, 32, and 34 are shown as being slightly bulged as compared to stent 10. In particular, the connector portions or crowns that are located generally at the middle of the length of the stent (e.g., in the area of crowns 29 of FIG. 1) alternate between those that are conical and those that are bulged around the circumference of the stent. That is, the stent is provided with three conical crowns that are arranged at approximately 120 degrees from each other and three bulged crowns that are also arranged at approximately 120 degrees from each other and are each also positioned to be approximately 60 degrees from adjacent conical crowns. When attaching a valve within the stent, each of the commissures of the valve can be attached in the area of one of the conical crowns, while the bulged crowns are positioned between the commissures and conical crowns. These bulged crowns can provide relief or distance between the tissue of the leaflet and the stent frame when the leaflets are in their open configuration. That is, the bulged crowns can help to prevent the leaflets from hitting or contacting the inner structure of the frame when the leaflets are open. In addition, the bulged crowns can help to protect the leaflets when the stent is retracted into a catheter sheath.

Figure 3:
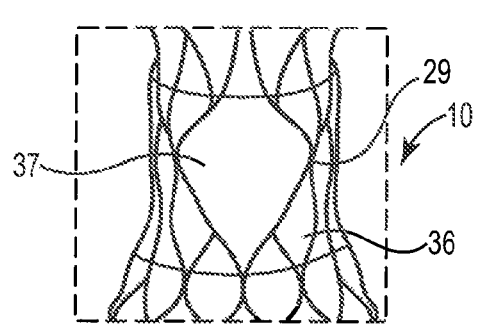
FIG. 3 is an enlarged front view of a portion of the stent illustrated in FIG. 1.

FIG. 3 is an enlarged portion of the central area of stent 10, which illustrates an exemplary manner of forming a bulged non-commissural crown or spar 29 during the process of manufacturing or forming the stent. In this embodiment, the stent can typically be made from a shape-memory type of material, although it is understood that other types of material(s) or combinations of materials can be utilized. In particular, this step of the forming process illustrates using a forming structure 36 that extends outwardly from a collar 37 to specifically push the crown area 29 outwardly relative to the collar 37. Once the shape setting of the stent is complete, these areas that have been pushed outwardly during the forming operation will at least slightly bulge or protrude outwardly as compared to the generally cylindrical shape of that portion of the stent.

Figure 4:
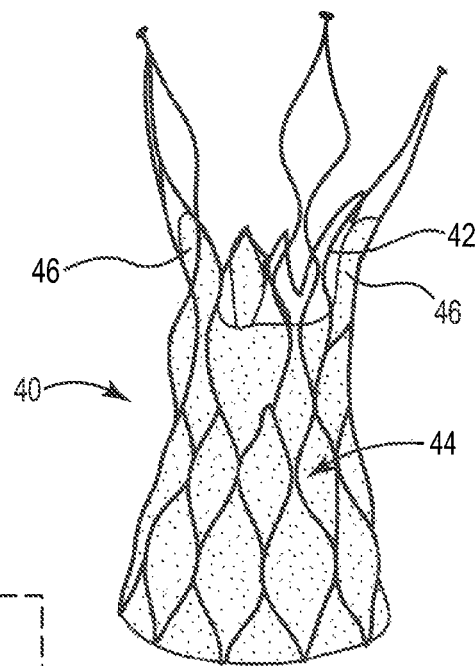
FIG. 4 is a front view of a stent embodiment of the type illustrated in FIG. 1 and further including a valve segment within its internal area.

FIG. 4 illustrates a transcatheter valve 40 that includes a stent 42 with a tissue valve 44 positioned within the internal area of the stent. The valve 40 is attached to the structure of the stent 42, which is similar in structure to stent 10 of FIG. 1. As shown, the tissue valve 44 is positioned closer to the end of stent 42 that has twelve diamond-shaped structures than to the end of stent 42 that includes six of such structures. Further, tissue valve 44 includes three leaflets, each of which extends between two adjacent commissures 46.

Figure 5:
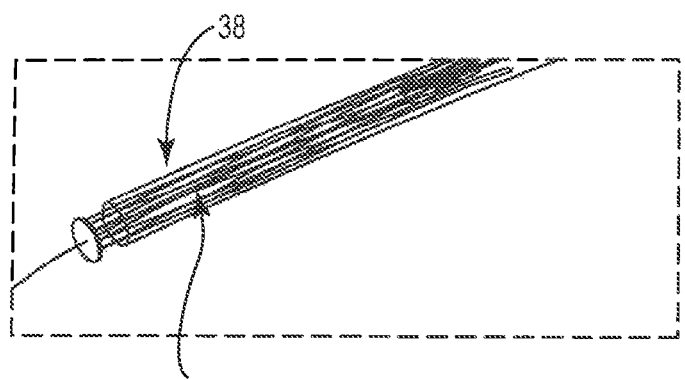
FIG. 5 is a front view of an in-vivo x-ray image of a stent of the invention positioned relative to a distal portion of a delivery system.

FIG. 5 is an in-vivo x-ray image of a stent 10 of the invention as it can be mounted relative to a distal portion of an exemplary delivery system 38. As shown, the stent 10 is positioned within a sheath near the distal tip of the delivery system 38. The chosen delivery system may include a number of different features and configurations, depending on the particular needs of the patient and/or the surgeon.

Figure 6:
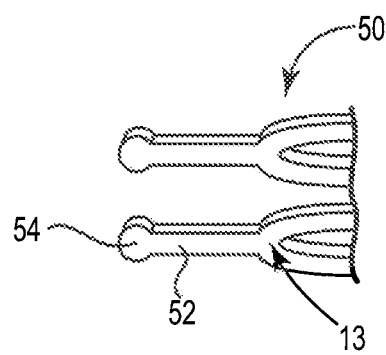
FIG. 6 is an enlarged front view of a portion of the stent illustrated in FIG. 1.
Figure 7:
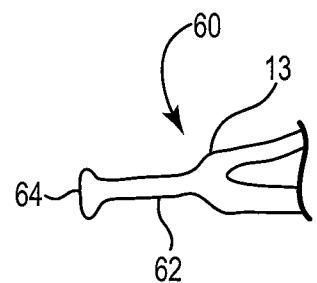
FIG. 7 is an enlarged front view of another portion of the stent illustrated in FIG. 1.

As described above relative to FIG. 1, stent 10 includes six crowns 13 at its end 12, where each of the crowns 13 includes a connector that extends from its end. Referring now to FIG. 6, one exemplary embodiment of a pair of connectors 50 at one end of a stent is illustrated, each of which includes an extending portion or post 52 that extends from the crown 13 at one end and that includes a half-dome portion 54 at its opposite end. The end of the stent having such connectors can include more or less than the two connectors illustrated in this figure. FIG. 7 illustrates another exemplary embodiment of a connector 60, which includes an extending portion or post 62 that extends from a crown 13 at one end and that includes a tee portion 64 at its opposite end. Additional configurations of these connectors are contemplated, wherein their structures are provided for engagement with a corresponding structure for implantation of the stent. For example, some portion of the delivery system that will be used to implant the device within a patient can include features that will allow for removable attachment of the stent to the delivery system.

Figure 8:
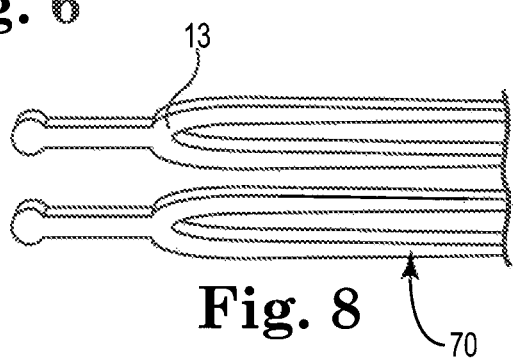
FIG. 8 is an enlarged front view of another portion of the stent illustrated in FIG. 1.

FIG. 8 is an enlarged front view of a portion of the stent 10 at its first end 12. In particular, crown 13 is shown with an extending connector and a strut portion 70. Strut portion 70 is tapered to provide for a reduced bending moment at the crown tips, but to maintain columnar support, which is particularly beneficial for deployment forces. Such a tapering of the strut portions can provide relief in the area where the number of crowns goes from a larger quantity to a smaller quantity (e.g., from 12 crowns to 6 crowns, as in the illustrated embodiment of FIG. 1). In particular, the tapering can reduce the effects of stresses that are present in the structure due to the differing number of crowns in different areas.

Figure 9:
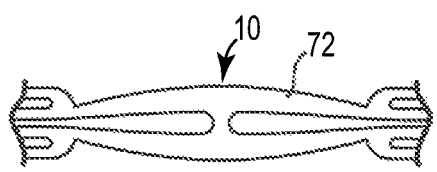
FIG. 9 is an enlarged front view of another portion of the stent illustrated in FIG. 1.

FIG. 9 is an enlarged front view of a portion of the stent 10 that is representative of the diamond-shaped structures that are generally in the area of row 23 of FIG. 1. However, FIG. 9 more particularly illustrates a tapered strut 72, which allows for a more tailored shape that matches the shape of the valve margin of attachment. The tapering further limits the stress applied to the adjacent crown area until the crown angle of the six crowns has opened adequately. This figure further includes bulged commissural spars or crowns for tissue relief, as is described above and illustrated relative to FIG. 3. The stent structure can further include a commissural pad that can be used for attaching and supporting the commissure of an attached valve during diastole (closure and closed loading). The pad can act as a supportive membrane when the commissure is attached orthogonally to the membrane that extends from the bottom of the diamond-shaped structure into the center position (i.e., along the center line).

Figure 10:
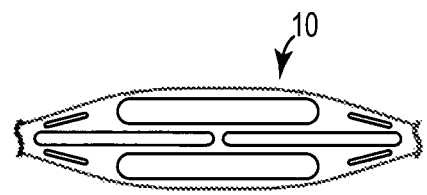
FIG. 10 is an enlarged front view of another portion of the stent illustrated in FIG. 1.
Figure 11:
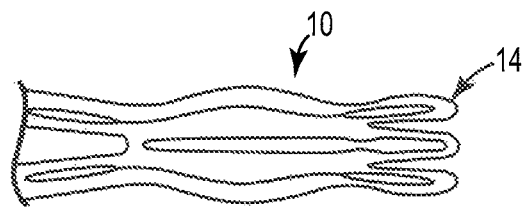
FIG. 11 is an enlarged front view of another portion of the stent illustrated in FIG. 1.

FIG. 10 is an enlarged front view of another portion of the stent 10 that is representative of the diamond-shaped structures that are generally in the area of rows 23 and 24 of FIG. 1. This FIG. 10 illustrates the radius of the top interior curve of an arch that is provided to maintain a crimp gap for better accommodation of seam and valve material. Due to this structure, this area can be the last to collapse during stent compression, thereby alleviating pressure on tissue that is attached in this area of the stent. The crown widths are shown as being tapered or variable and the crowns are offset, thereby mitigating the potential for buckling and minimizing the tissue pressure during the crimping or stent compression procedure FIG. 11 is an enlarged front view of yet another portion of the stent 10, which illustrates an area of the structure near its second end 14. In this area, the strut width, radius, and strut length (which includes an increased angle) are provided to enlarge the crimped cell size, thereby accommodating tissue of a valve and the sutures used for attaching the valve to the stent.

Figure 12:
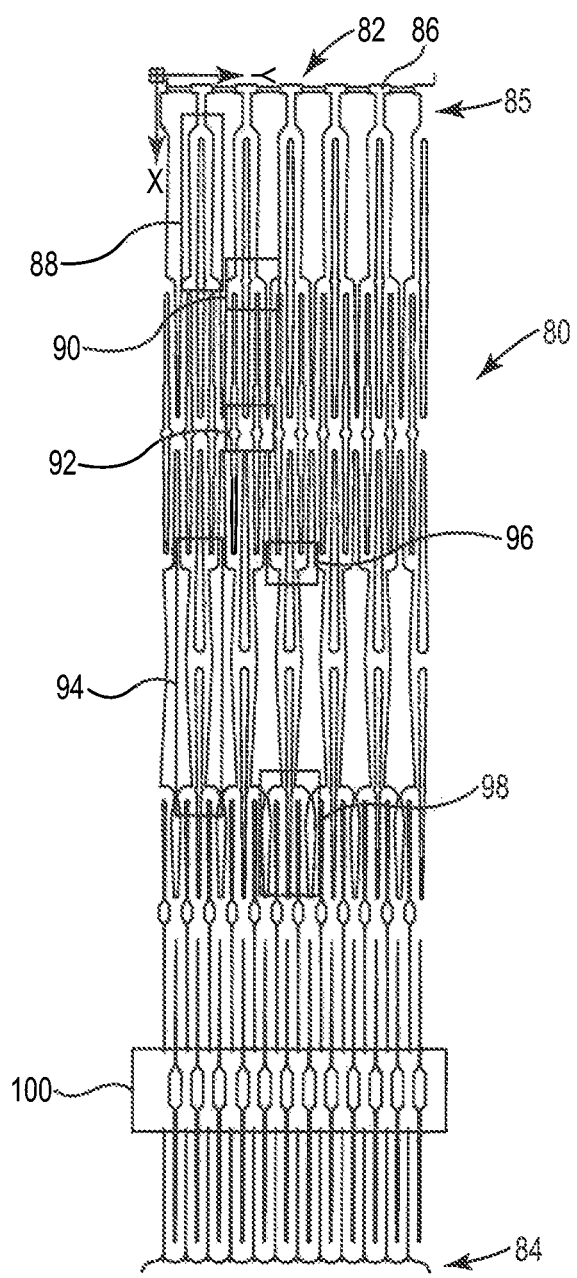
FIG. 12 is a front view of an embodiment of a wire structure or blank that can be used for a stent of the type illustrated in FIG. 1.

FIG. 12 illustrates an exemplary wire structure or blank 80 for use as a stent embodiment of the type illustrated in FIG. 1, which additionally illustrates some of the features discussed above relative to FIGS. 6-11. The wire structure 80 can be formed into a cylinder and attached along an intersection line to provide a stent generally of the type illustrated in FIG. 1. In the embodiment of FIG. 12, wire structure 80 comprises a single piece construction that can be provided via a number of manufacturing methods, such as by stamping, laser cutting, and the like. It is also possible, however, that the wire structure consists of multiple wire segments attached to each other in various locations to make up this structure. In any case, this wire structure includes a first end 82 and opposite second end 84. First end 82 includes multiple connectors 85, which are shown in this figure as having tee-shaped ends 86 of the type illustrated in FIG. 7, for example, although it is contemplated that the ends of the connectors can be configured in another way, such as for engagement with a particular corresponding structure of a delivery system.

Wire structure 80 further includes an area 88 that is generally illustrated in FIG. 8, as discussed above. This area provides a tapered strut for a reduced bending moment on the crown tips while maintaining the columnar support for the stent, which can be important during deployment of the stent. Wire structure 80 also includes an area 90 that provides a reduced crown offset, radius and strut width for a lower crimp profile in an area where more buckling can be present. It is noted that in this context, strut width is the circumferential width of the strut, while the strut thickness is the radial thickness, which corresponds to the wall thickness of a tube. In addition, wire structure 80 includes an area 92 that provides a hinge design single connector pivot, which provides for increased "decoupling" behavior from arch angle depression.

With continued reference to FIG. 12, wire structure 80 includes area 94 that has tapered struts that are tailored for margin of attachment shape and reduced buckling, as is generally illustrated in FIG. 9. Wire structure 80 further includes areas 96 and 98, which are generally illustrated in FIG. 10. Areas 96 and 98 include an interior arch curve that can maintain the crimp gap for better accommodation of seam and valve material, along with other features described above relative to FIG. 10. Finally, wire structure 80 includes an area 100 spaced from the second end 84 of the stent 80. Area 100 is a connector region that provides for decreased density and can also include a radiopaque feature to aid in targeting through a metallic sheath, as is illustrated in the x-ray image of FIG. 4, for example.

Figure 13:
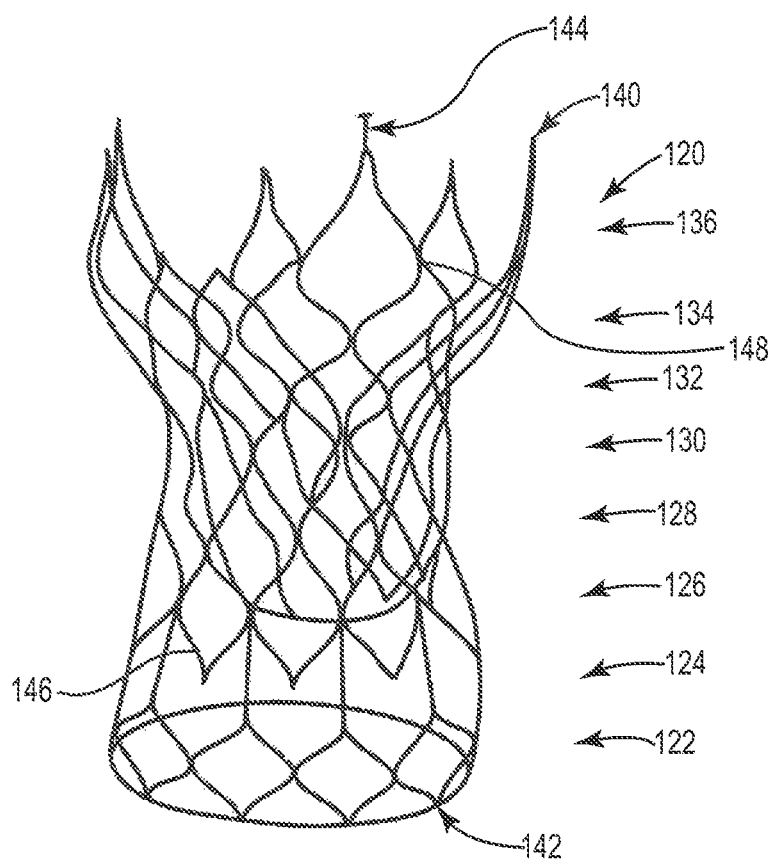
FIG. 13 is a front view of another embodiment of a stent in accordance with the invention.
Figure 14:
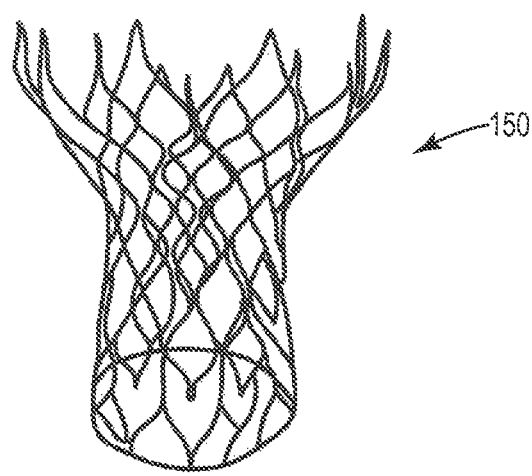
FIG. 14 is a front view of another exemplary stent of the type illustrated in FIG. 13.

FIGS. 13 and 14 illustrate another alternative embodiment of a stent 120. Stent 120 includes a first end 140 having six crowns and a second end 142 having twelve crowns. In this embodiment, the first end 140 may be considered to be the outflow end of the stent and the second end 142 may be considered to be the inflow end of the stent. At least one of the stent crowns at the first end 140 includes a crown end 144 that may include a half-dome or tee connector, for example. These crown ends 144 can be used for engagement of the stent with a delivery system, for example. It is contemplated that each of the crown ends 144 at the second end includes a half-dome or tee connector, as shown, or that only some of the crowns include such a connector. The size and shape of the crown ends 144 and their extending can all be the same on a single stent, or they can have different sizes and/or shapes.

The structure of stent 120 includes a series of adjacent rows of diamond-shaped structures. In particular, stent 120 includes a row 122 of such structures at second end 142 of the stent, wherein this particular embodiment includes twelve of the diamond-shaped structures in row 122. A row 124 of generally diamond-shaped structures is adjacent to row 122, where each of these structures includes a V-shaped portion from which two vertical wire portions extend. These vertical wire portions extend generally in the direction of a longitudinal axis of the stent. The vertical wire portions may alternatively be referred to as "peak-to-valley connectors", as each of these wire portions extends between a "peak" of a structure of row 122 and a "valley" of a structure of row 126. These peak-to-valley connectors help the segments to act more independently from each other, which may also be referred to as "de-coupling behavior". That is, if the device is compressed at the inflow side, the device is structurally unchanged at some point superior to this point and is changed to some degree in between these points. With such a structure, the device can accommodate a large degree of "non-circularity" (e.g., an elliptic or oval shape) relative to the inflow or lower portion of the structure and protect the valve portion from distortion by keeping it as circular as possible. The de-coupling behavior can also be helpful when retracting the stent into a sheath, in that it helps to keep the segments independent from each other while in a closed cell configuration.

Lower V-shaped portions of the structures of row 124 coincide with the upper wire portions of two adjacent diamond-shaped structures of row 122. A row 126 of wire structures is adjacent to row 124 and includes twelve diamond shaped structures, which are adjacent to each other around the circumference of the stent 120. A lower V-shaped portion of each of these structures of row 126 extends generally into the open area between the vertical wire portions of the adjacent row 124.

The next four rows of generally diamond-shaped structures are illustrated as rows 128, 130, 132, 134, each of which includes twelve diamond-shaped structures, and where each of the structures shares two sides with a diamond-shaped structure of an adjacent row. The final row of structures is row 136, which is positioned at first end 140 of stent 120. Row 136 includes six diamond-shaped structures, as described above.

Figure 16:
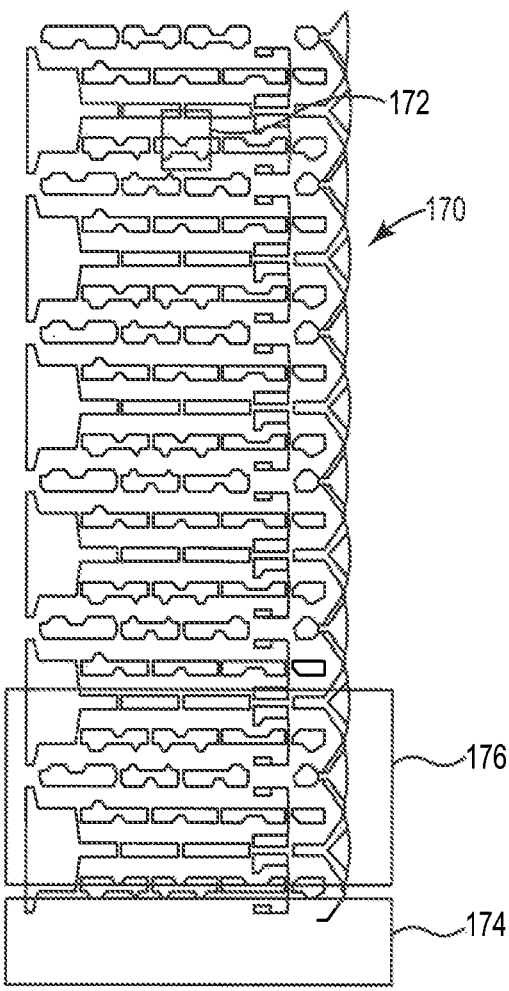
FIG. 16 is a schematic illustration of the stent frame of FIG. 13.

Stent 120 further includes areas of crown reduction, one of which is generally located at area 148. The reduced number of crowns in this area provides for fewer points of attachment to the delivery system, which can result in a smaller probability for failed release from the delivery system when it is desirable for such a release. This area is also designated as an area 172 on the schematic representation 170 of stent 120 illustrated in FIG. 16. With further reference to FIG. 16, the skirt area described herein is illustrated generally as an area 174. In addition, a portion of the stent illustrated generally as an area 176 is the area of the stent that can be considered to have a conformable open-cell structure, which is the area that includes the peak-to-valley connectors described above relative to stent 120.

Referring again to FIG. 13, stent 120 is illustrated in its expanded or partially expanded condition. This illustrated condition is intended to represent the stent condition when it is implanted within the anatomy of a patient. In this expanded condition, stent 120 is generally configured to have a relatively small diameter adjacent to the second end 142 as compared to the diameter of its first end 140. End 142 can have the same or different diameter in its expanded condition as the diameter of the central area of the stent (e.g., in the area of rows 128, 130, etc.), wherein this figure illustrates the end 142 as being slightly flared or tapered outwardly as compared to the central area. End 140 is flared outwardly (i.e., away from the central longitudinal axis of the stent), which can prevent or minimize leakage between the implanted heart valve and the native annulus and/or to provide a physical and/or visual docking feature to secure the stent against a wall of a vessel or opening in the heart to prevent migration of the stent, for example.

FIG. 13 further illustrates a "margin of attachment" 146, which is an exemplary line along which a valve can be attached to the stent 120. As shown, the margin of attachment 146 is generally U-shaped and intersects with stent wires and intersection points of two or more stent wires along its length. This margin of attachment 146 is only one exemplary placement of the valve structure, where the various wire structures of the stent can be adjusted to provide different locations for the various components, which will thereby change the positioning and shape of the margin of attachment.

Stent 120 further includes a skirt support at its second end 142, which is provided by the lowest level of V-shaped structures. In particular, the skirt support includes a non-scaffolding segment of high-crown angle elements that help to increase the effective length of the skirt. That is, the skirt support area provides support to the skirt material basically for more effective sealing, thereby minimizing or eliminating paravalvular leakage in this area.

FIG. 14 illustrates a similar stent structure to that shown in FIG. 13, except that the second end of this stent 150 has a diameter that is the same or similar to that of the central region of the stent. That is, the stent 150 is provided with less contours along its length than the stent 120 of FIG. 13.

Figure 15:
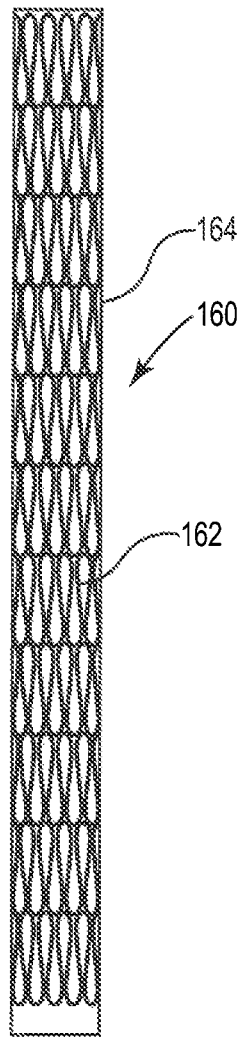
FIG. 15 is a front view of the stent illustrated in FIG. 13 in its compressed condition and as positioned relative to a delivery system.

FIG. 15 illustrates a portion of a delivery system 160, onto which is loaded a stent 162. Stent 162 includes a series of wires or wire segments and can have the same or a similar structure to that of stent 120 illustrated in FIG. 13. Stent 162 is illustrated in its compressed or crimped condition within a sheath 164 of the delivery system 160. As is described in further detail below, the stent may be delivered to its desired location within the patient using this delivery system, and then the sheath 164 can be retracted from the stent 162, thereby letting it expand to its deployed condition. It is understood that this type of delivery system is appropriate for use when the stent 162 is made of a shape memory material; however, stent 162 may instead be made of a material that is not self-expanding such that the delivery system includes an expandable balloon that causes the expansion of the stent to its deployed condition.

Figure 17:
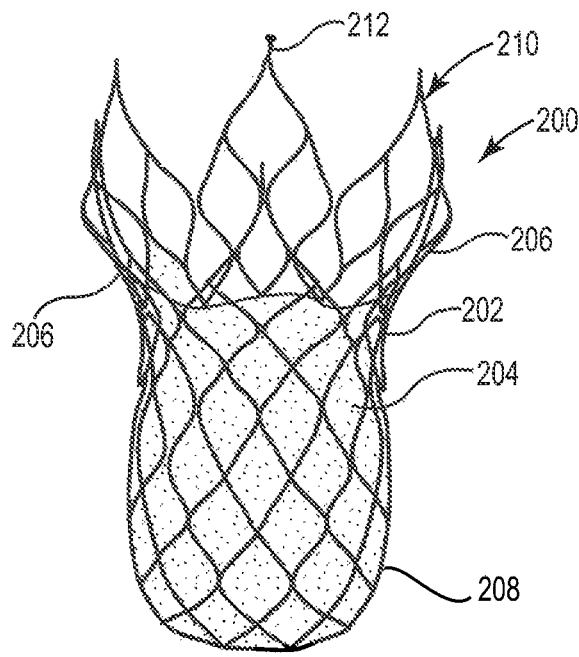
FIG. 17 is a perspective view of another embodiment of a stent of the invention with a valved segment positioned within its internal area.
Figure 19:
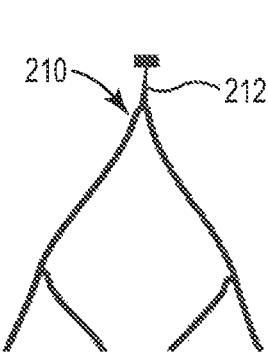
FIG. 19 is an enlarged front view of a portion of the stent illustrated in FIG. 17.
Figure 18:
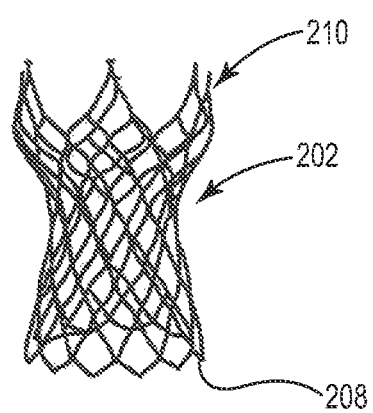
FIG. 18 is a front view of the stent of FIG. 17 without a valved segment within its internal area.

FIGS. 17 and 18 illustrate another exemplary stent of the invention, wherein FIG. 18 illustrates a stent 202 without a valve and FIG. 17 illustrates a stented valve 200 that comprises stent 202 with a valve 204 positioned within its interior area. Stent 202 includes a first end 210 and an opposite second end 208. Connectors 212 extend from each of the peaks at this first end 210, wherein each connector 212 has an end that is configured to engage with a portion of a delivery system (e.g., the tee connector end illustrated in the enlarged view of FIG. 19). Valve 204, which is attached within the interior area of stent 202, includes three commissures 206 and leaflets that extend between each pair of adjacent commissures 206.

Stent 202 has a similar shape to the stent 120 of FIG. 13; however stent 202 does not have the same peak-to-valley connectors that are part of the structure of the stent 120. Rather, stent 202 includes a generally regular diagonal crisscross wire pattern along its entire length, with multiple "cells" that are generally defined by wire segments. As with the other stent embodiments described above, stent 202 includes twelve generally diamond-shaped structures at its second end 208 and six diamond-shaped structures at its first end 210. However, this stent 202 does not include an area in the central area of the stent with reduced strut density, but instead comprises a stent structure with twelve generally diamond-shaped structures in each row besides the row at the first end 210. Stent 202 further includes a bulbous or flared shape adjacent to its first end 210.

Figure 20:
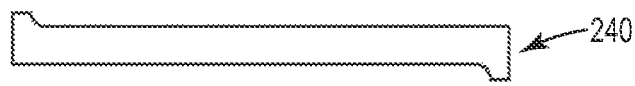
FIGS. 20 and 21 are front views of exemplary tapered struts of the type that can be used with the stent embodiment of FIGS. 17 and 18.
Figure 21:
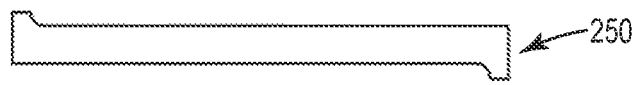

FIGS. 20 and 21 illustrate exemplary configurations of tapered struts 240, 250, respectively, which can be used in various areas of the stent 202, as desired. These configurations can provide for stress flow control during shape-set induced geometry, loading, and unloading behavior.

Figure 22:
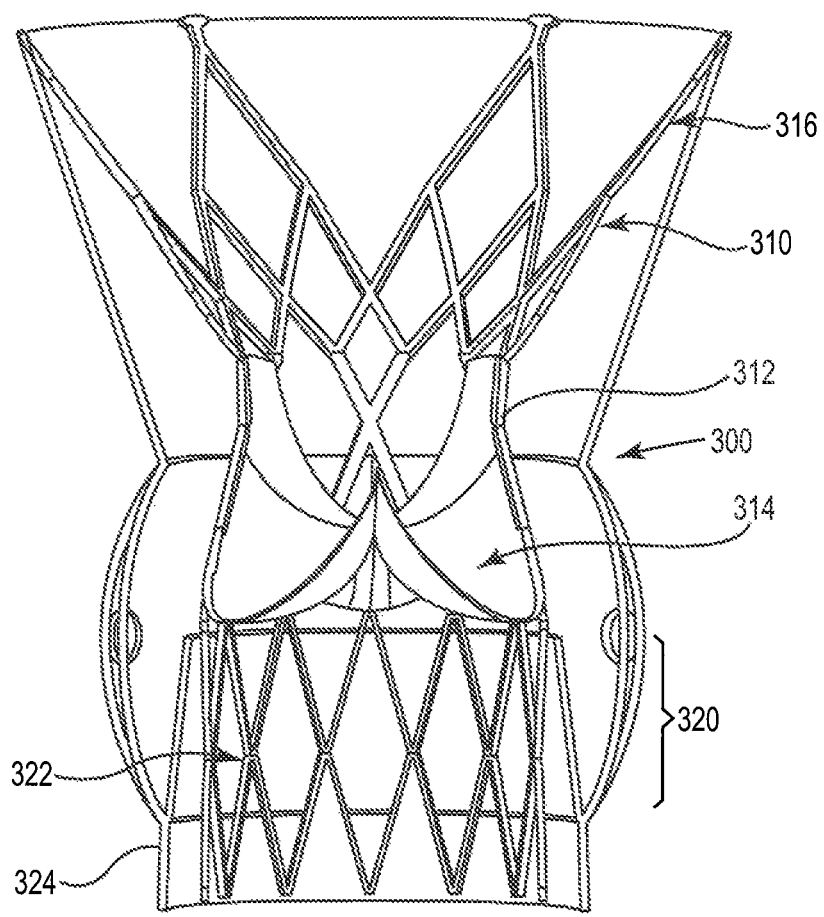
FIG. 22 is a front view of a stent of the type illustrated FIG. 1 as positioned within a model of a portion of the anatomy of a patient and including a valve positioned within the stent.
Figure 23:
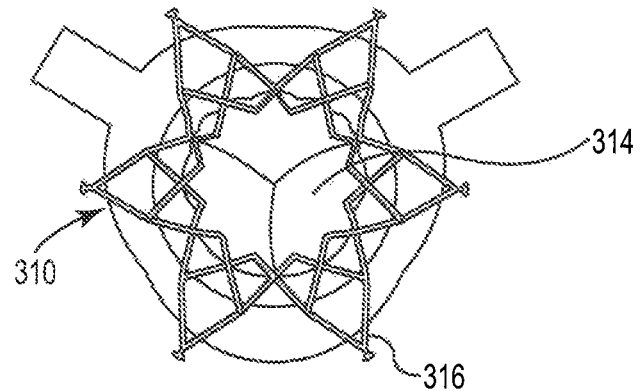
FIG. 23 is a top view of the stented valve of FIG. 22 positioned within a model of a portion of the anatomy of a patient.
Figure 24:
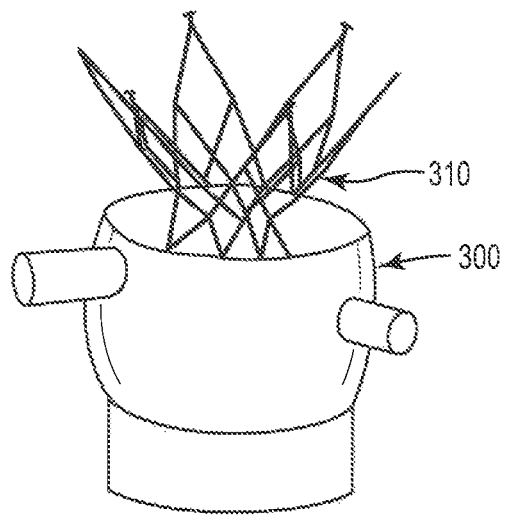
FIG. 24 is a front perspective view of the stented valve of FIG. 22 positioned within a model of a portion of the anatomy of a patient, with a portion of a anatomical model cut away to more clearly illustrate the stent.
Figure 25:
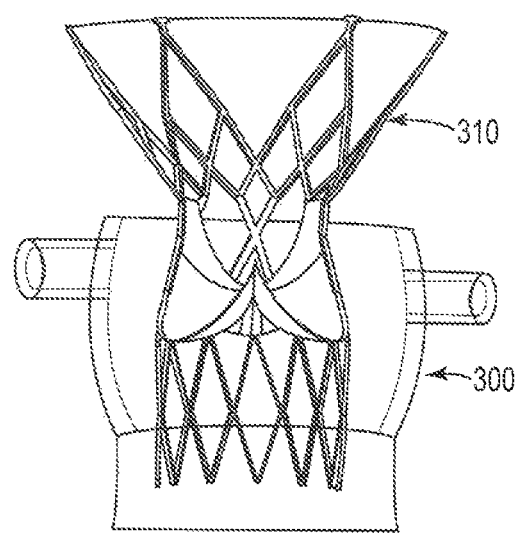
FIG. 25 is a front view of the stented valve within the anatomical model of FIG. 24.
Figure 26:
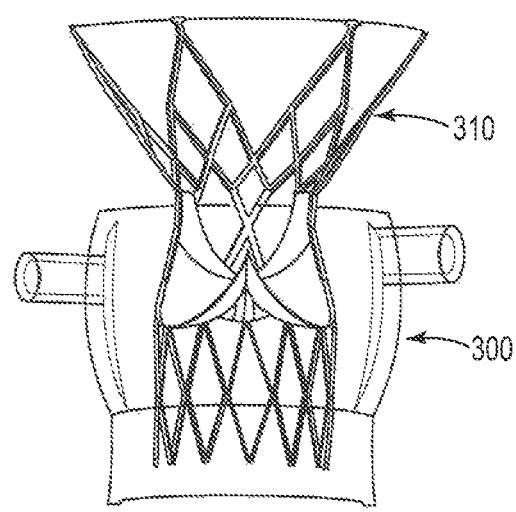
FIG. 26 is another front view of the stented valve within the anatomical model of FIGS. 24 and 25.

FIG. 22 illustrates a valved stent embodiment 310, which includes a stent 312 similar to stent 10 of FIG. 1, along with a valve 314 positioned within the inner area of the stent 312. This valved stent 310 is illustrated as it can be positioned relative to an aortic valve position 300 of a heart. Stent 312 includes six stent crowns at one end and twelve stent crowns at the opposite end, as described above. The valved stent 310 is positioned with its central area located generally in the bulbous area of the aorta. A flared area 316 at one end extends into the ventricle, for example, in order to help anchor the valved stent 310 in place. The flared area 316 is preferably positioned in a location where it does not disrupt the native anatomical function. That is, the flared area 316 should not interfere with the mitral valve anterior leaflet and should not apply pressure to the septum in the area of the conduction system bundle branch. Again, it is also preferable that the central portion of the valved stent 310 does not contact the native aortic sinus region, in order to minimize the potential for coronary occlusion or obstruction.

This exemplary valved stent 310, along with the other stents of the invention, can be positioned in a number of different locations relative to the native leaflets, while keeping the various restrictions discussed above in mind. In particular, the native leaflet area is designated in FIG. 22 as reference number 320. In this Figure, the valved stent 310 is shown with the bottom of its valve area positioned above the native leaflet area 320 and therefore may be said to be in a "supra-valvular" position relative to the native leaflet area 320. However, it is contemplated that the valved stent 310 may instead be located in a "supra-annular" position, where the bottom of the valve area of the valved stent is instead located approximately in the area designated by reference number 322, which is generally in the center of the native leaflet area 320. It is further contemplated that the valved stent may instead be located in a orthotopic position relative to the native anatomy, where the bottom of the valve area of the valved stent is instead located approximately in the area designated by reference number 324, which is at the bottom of or below the native leaflet area 320.

FIGS. 23-26 illustrate multiple views of the valved stent 310 positioned relative to the aortic valve position 300 of a heart. For clarity of illustration, these figures have a portion of the anatomical model cut away to better view the stent and its attached valve.

Delivering any balloon-expandable stents of the invention to the implantation location can be performed percutaneously. In general terms, this includes providing a transcatheter assembly, including a delivery catheter, a balloon catheter, and a guide wire. Some delivery catheters of this type are known in the art, and define a lumen within which the balloon catheter is received. The balloon catheter, in turn, defines a lumen within which the guide wire is slideably disposed. Further, the balloon catheter includes a balloon that is connected to an inflation source. It is noted that if the stent being implanted is a self-expanding type of stent, a balloon would not be needed and a sheath or other restraining means would instead be used for maintaining the stent in its compressed state until deployment of the stent, as described herein. In any case, for a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of the transcatheter assembly.

Prior to delivery, the stent is mounted over the balloon in a contracted state to be as small as possible without causing permanent deformation of the stent structure. As compared to the expanded state, the stent structure is compressed onto itself and the balloon, thus defining a decreased inner diameter as compared to an inner diameter in the expanded state. While this description is related to the delivery of a balloon-expandable stent, the same general procedures are applicable to a self-expanding stent, where the delivery system would not include a balloon, but would preferably include a sheath or some other type of structure for maintaining the stent in a compressed condition until its deployment.

With the stent mounted to the delivery system, the transcatheter assembly is delivered through a percutaneous opening in the patient via the delivery catheter. The implantation location is located by inserting a guide wire into the patient, which glide wire extends from a distal end of the delivery catheter, with the balloon catheter otherwise retracted within the delivery catheter. The balloon catheter is then advanced distally from the delivery catheter along the guide wire, until the balloon and stent is positioned in the area of the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the invention, the stent includes a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

Once the stent is properly positioned, the balloon catheter is operated to inflate the balloon, thus transitioning the stent to an expanded state. Alternatively, where the support structure is formed of a shape memory material, the sheath or other structure of the delivery system can be removed or displaced relative to the stent, thereby allowing the stent to self-expand to its expanded state.

One or more markers on the valve, along with a corresponding imaging system (e.g., echo, MRI, etc.) can be used with the various repositionable delivery systems described herein in order to verify the proper placement of the valve prior to releasing it from the delivery system. A number of factors can be considered, alone or in combination, to verify that the valve is properly placed in an implantation site, where some exemplary factors are as follows: (1) lack of paravalvular leakage around the replacement valve, which can be advantageously examined while blood is flowing through the valve since these delivery systems allow for flow through and around the valve; (2) optimal rotational orientation of the replacement valve relative to the coronary arteries; (3) the presence of coronary flow with the replacement valve in place; (4) correct longitudinal alignment of the replacement valve annulus with respect to the native patient anatomy; (5) verification that the position of a sinus region of the replacement valve does not interfere with native coronary flow; (6) verification that a sealing skirt is aligned with anatomical features to minimize paravalvular leakage; (7) verification that the replacement valve does not induce arrhythmias prior to final release; and (8) verification that the replacement valve does not interfere with function of an adjacent valve, such as the mitral valve.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described and illustrated herein, but only by the structures described by the language of the claims and the equivalents of those structures.

The invention claimed is:

1. A prosthetic valve comprising:
a wire frame comprising a generally tubular body portion, an interior area, a longitudinal axis, a first end comprising a plurality of crowns, and a second end comprising a greater number of crowns than the first end, wherein the wire frame comprises a plurality of adjacent rows of diamond-shaped structures extending between the first and second ends
wherein a first intermediate row of diamond-shaped structures is spaced from both the first and second ends of the wire frame, wherein the first intermediate row comprises a plurality of diamond-shaped structures that are each spaced from each other by a gap distance around the tubular body portion of the wire frame,
wherein a second intermediate row of diamond-shaped structures is spaced from both the first and second ends of the wire frame, wherein the second intermediate row comprises a plurality of diamond-shaped structures that are each spaced from each other by a gap distance around the tubular body portion of the wire frame,
wherein respective peaks of each diamond-shaped structure of the first intermediate row and respective valleys of each diamond-shaped structure of the second intermediate row form a respective connection portion between the respective peaks and valleys such that the wire frame includes a plurality of connection portions, wherein the connection portions also form a portion of a large-cell row of diamond-shaped structures,
wherein some of the plurality of connection portions are bulged radially outwardly relative to the other of the plurality of connection portions to form bulged connection portions, wherein bulges of the bulged connection portions are located between the respective peaks of the first intermediate row and respective valleys of the second intermediate row; and
a valve structure attached within the interior area of the wire frame, the valve structure comprising a plurality of leaflets.

2. The prosthetic valve of claim 1, wherein a first row of the plurality of rows comprises a plurality of diamond-shaped structures extending around the tubular body portion of the wire frame, wherein each of the diamond-shaped structures includes a curved intersection area that extends from a curved intersection area of an adjacent diamond-shaped structure.

3. The prosthetic valve of claim 2, wherein each of the diamond-shaped structures of the first row comprises a first peak spaced along a length of the wire frame from a second peak, wherein at least one of the first and second peaks comprises a curved radius portion.

4. The prosthetic valve of claim 3, wherein the first peak and second peak are spaced from each other in a direction that is generally parallel to a longitudinal axis of the wire frame.

5. The prosthetic valve of claim 2, wherein each curved intersection area comprises a point from which two adjacent wire segments of a modified diamond-shaped structure extend.

6. The prosthetic valve of claim 5, further comprising a connector portion at the point from which two adjacent wire segments extend.

7. The prosthetic valve of claim 2, wherein at least one of the curved intersection areas protrudes outwardly relative to the tubular body portion of the wire frame.

8. The prosthetic valve of claim 1, wherein the large-cell row of diamond-shaped structures is adjacent to the first and second intermediate rows of structures, wherein the large-cell row comprises a plurality of adjacent diamond-shaped structures that extend directly from each other around the tubular body portion of the wire frame.

9. The prosthetic valve of claim 8, wherein each of the structures of the large-cell row comprises a larger open area than an open area of each of the structures of the first and second intermediate rows.

10. The prosthetic valve of claim 1, wherein the first and second ends of the wire frame each have an outer circumference that is larger than an outer circumference of a central area of the wire frame, wherein the central area is longitudinally spaced between the first and second ends.

11. The prosthetic valve of claim 1, wherein the first end of the wire frame comprises an outflow end of the frame and wherein the second end of the wire frame comprises an inflow end of the frame.

12. The prosthetic valve of claim 1, further comprising a connector extending from at least one of the crowns of at least one of the first and second ends of the wire frame.

13. The prosthetic valve of claim 1, wherein the wire frame is radially self-expandable.

14. The prosthetic valve of claim 1, wherein the first intermediate row of diamond-shaped structures, the second intermediate row of diamond-shaped structures, and the large-cell row of diamond-shaped structures all include the same number of diamond-shaped structures.

15. The prosthetic valve of claim 1, wherein half of the plurality of connection portions are bulged radially outwardly relative to the other half of the plurality of connection portions.

16. The prosthetic valve of claim 15, wherein the valve structure includes a plurality of commissures where adjacent leaflets are joined, wherein each commissure of the valve structure is attached to a respective non-bulged connection portion.

17. The prosthetic valve of claim 1, wherein the valve structure includes a plurality of commissures where adjacent leaflets are joined, wherein each commissure of the valve structure is attached to a respective non-bulged connection portion.

18. The prosthetic valve of claim 17, wherein each non-bulged connection portion is disposed between two adjacent bulged connection portions.

19. A prosthetic valve comprising:
a wire frame comprising a generally tubular body portion, an interior area, a longitudinal axis, a first end comprising a plurality of crowns, and a second end comprising a greater number of crowns than the first end, wherein the wire frame comprises a plurality of adjacent rows of diamond-shaped structures extending between the first and second ends
wherein a first intermediate row of diamond-shaped structures is spaced from both the first and second ends of the wire frame, wherein the first intermediate row comprises a plurality of diamond-shaped structures that are each spaced from each other by a gap distance around the tubular body portion of the wire frame,
wherein a second intermediate row of diamond-shaped structures is spaced from both the first and second ends of the wire frame, wherein the second intermediate row comprises a plurality of diamond-shaped structures that are each spaced from each other by a gap distance around the tubular body portion of the wire frame,
wherein respective peaks of each diamond-shaped structure of the first intermediate row and respective valleys of each diamond-shaped structure of the second intermediate row are connected to each other to form a respective connection portion such that the wire frame includes a plurality of connection portions, wherein the connection portions also form a portion of a large-cell row of diamond-shaped structures,
wherein some of the plurality of connection portions are bulged radially outwardly relative to the other of the plurality of connection portions to form bulged connection portions, wherein the respective peaks of the first intermediate row and the respective valleys of the second intermediate row of the connection portions that form the bulged connection portions are bulged relative the respective peaks and valleys of the non-bulged connection portions; and
a valve structure attached within the interior area of the wire frame, the valve structure comprising a plurality of leaflets.

20. The prosthetic valve of claim 19, wherein the valve structure includes a plurality of commissures where adjacent leaflets are joined, wherein each commissure of the valve structure is attached to a respective non-bulged connection portion.

* * * * *